US008808330B2

(12) United States Patent
Biedermann et al.

(10) Patent No.: US 8,808,330 B2
(45) Date of Patent: Aug. 19, 2014

(54) ANCHORING ELEMENT AND STABILIZATION DEVICE FOR THE DYNAMIC STABILIZATION OF VERTEBRAE OR BONES USING SUCH ANCHORING ELEMENTS

(75) Inventors: Lutz Biedermann, VS-Villingen (DE); Jürgen Harms, Karlsruhe (DE); Wilfried Matthis, Weisweil (DE)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 1001 days.

(21) Appl. No.: 11/070,873

(22) Filed: Mar. 2, 2005

(65) Prior Publication Data

US 2005/0203516 A1    Sep. 15, 2005

Related U.S. Application Data

(60) Provisional application No. 60/550,008, filed on Mar. 3, 2004.

(30) Foreign Application Priority Data

Mar. 3, 2004    (DE) .................... 10 2004 010 380

(51) Int. Cl.
*A61B 17/70*    (2006.01)

(52) U.S. Cl.
USPC ............................................. 606/264

(58) Field of Classification Search
USPC .................... 606/72, 73, 266–278
See application file for complete search history.

(56) References Cited

U.S. PATENT DOCUMENTS

| 4,946,458 | A |   | 8/1990 | Harms et al. ............... 606/61 |
| 5,176,680 | A |   | 1/1993 | Vignaud et al. |
| 5,190,543 | A |   | 3/1993 | Schläpfer |
| 5,207,678 | A | * | 5/1993 | Harms et al. ............ 606/267 |
| 5,254,118 | A | * | 10/1993 | Mirkovic .................. 606/61 |
| 5,474,555 | A |   | 12/1995 | Puno et al. ............... 606/73 |
| 5,480,401 | A | * | 1/1996 | Navas ..................... 606/256 |
| 5,505,731 | A | * | 4/1996 | Tornier ................... 606/61 |
| 5,628,740 | A |   | 5/1997 | Mullane |
| 5,669,911 | A | * | 9/1997 | Errico et al. ............. 606/264 |

(Continued)

FOREIGN PATENT DOCUMENTS

| EP |       242 708 A2 | 4/1987 |
| EP |       483 242 B1 | 5/1995 |
| WO | WO 03/068083 A1 | 8/2003 |

OTHER PUBLICATIONS

European Searh Report dated Jul. 27, 2005 for parallel European application EP 05 00 3913, 5 sheets.

*Primary Examiner* — Mary Hoffman
(74) *Attorney, Agent, or Firm* — Christie, Parker & Hale, LLP

(57) ABSTRACT

An anchoring element for a stabilization device for bones or vertebrae, with which a bone or vertebra can be connected to a rod-shaped element is described. By providing for at least one degree of rotational freedom between the rod and an anchoring element that is firmly connected to the bone or vertebra, the transfer of torque (M) onto the anchoring element and can be prevented as well as loosening or even separation of the bone anchoring element from the bone or vertebra. Moreover, the invention provides a stabilization device, in which such bone anchoring elements are used.

8 Claims, 8 Drawing Sheets

(56) References Cited

U.S. PATENT DOCUMENTS

| | | | |
|---|---|---|---|
| 5,733,284 A | 3/1998 | Martin | 606/61 |
| 5,797,911 A * | 8/1998 | Sherman et al. | 606/270 |
| 5,817,094 A * | 10/1998 | Errico et al. | 606/264 |
| 5,879,350 A * | 3/1999 | Sherman et al. | 606/270 |
| 5,882,350 A * | 3/1999 | Ralph et al. | 606/278 |
| 5,938,663 A * | 8/1999 | Petreto | 606/61 |
| 5,984,924 A * | 11/1999 | Asher et al. | 606/61 |
| 5,989,254 A * | 11/1999 | Katz | 606/308 |
| 6,053,917 A * | 4/2000 | Sherman et al. | 606/270 |
| 6,063,090 A * | 5/2000 | Schlapfer | 606/270 |
| 6,113,601 A * | 9/2000 | Tatar | 606/266 |
| 6,132,434 A * | 10/2000 | Sherman et al. | 606/78 |
| 6,273,888 B1 * | 8/2001 | Justis | 606/272 |
| 6,280,442 B1 * | 8/2001 | Barker et al. | 606/60 |
| 6,368,321 B1 | 4/2002 | Jackson | |
| 6,379,357 B1 * | 4/2002 | Bernstein et al. | 606/246 |
| 6,471,705 B1 * | 10/2002 | Biedermann et al. | 606/271 |
| 6,716,214 B1 * | 4/2004 | Jackson | 606/266 |
| 6,800,079 B2 * | 10/2004 | Reed | 606/73 |
| 6,835,196 B2 * | 12/2004 | Biedermann et al. | 606/308 |
| 7,722,652 B2 * | 5/2010 | Justis et al. | 606/267 |
| 2002/0143341 A1 | 10/2002 | Biedermann et al. | |
| 2003/0032957 A1 * | 2/2003 | McKinley | 606/61 |
| 2003/0045879 A1 | 3/2003 | Minfelde et al. | |
| 2003/0073996 A1 | 4/2003 | Doubler et al. | |
| 2004/0097933 A1 * | 5/2004 | Lourdel et al. | 606/61 |
| 2004/0267264 A1 * | 12/2004 | Konieczynski et al. | 606/73 |

* cited by examiner

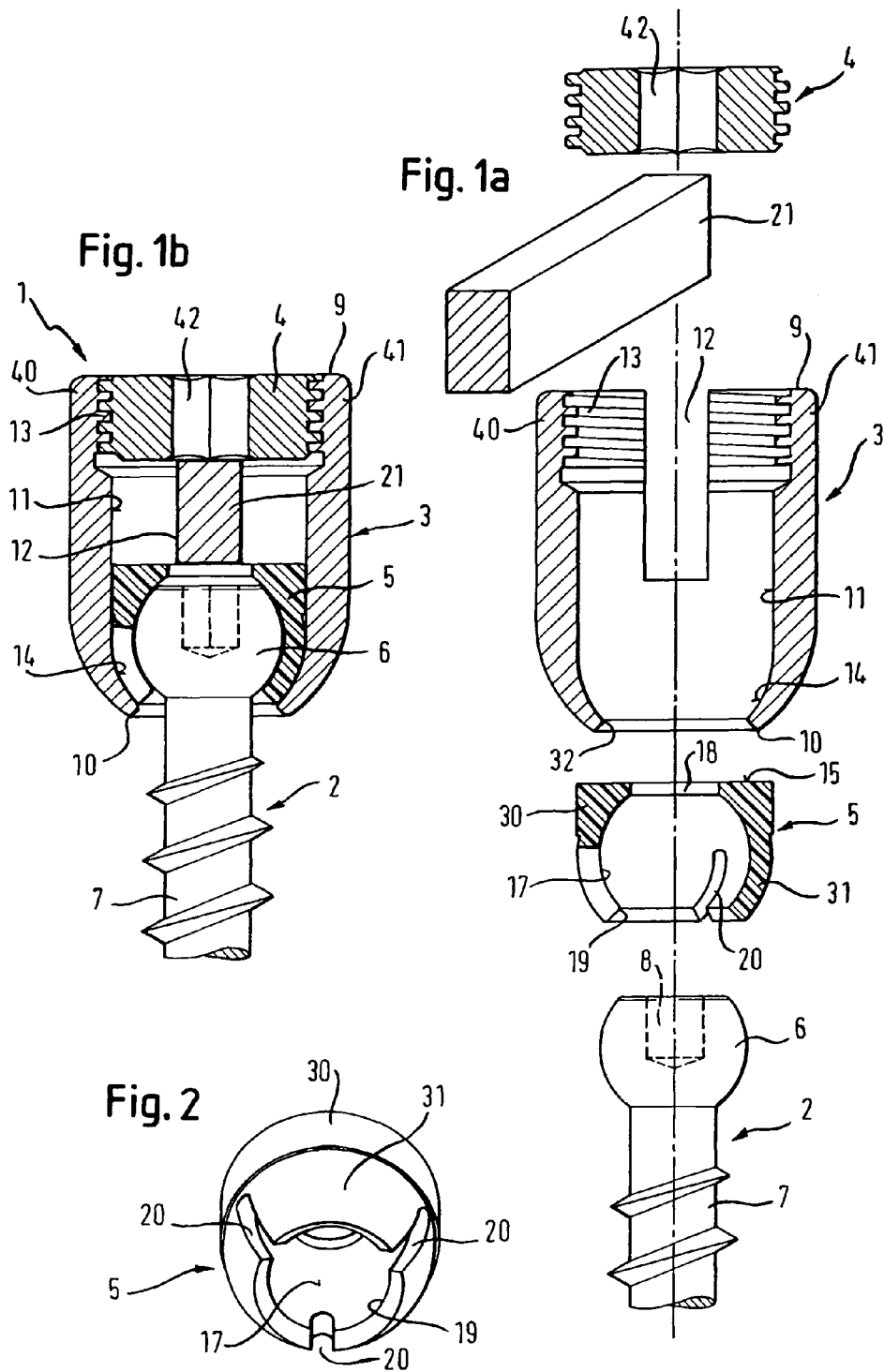

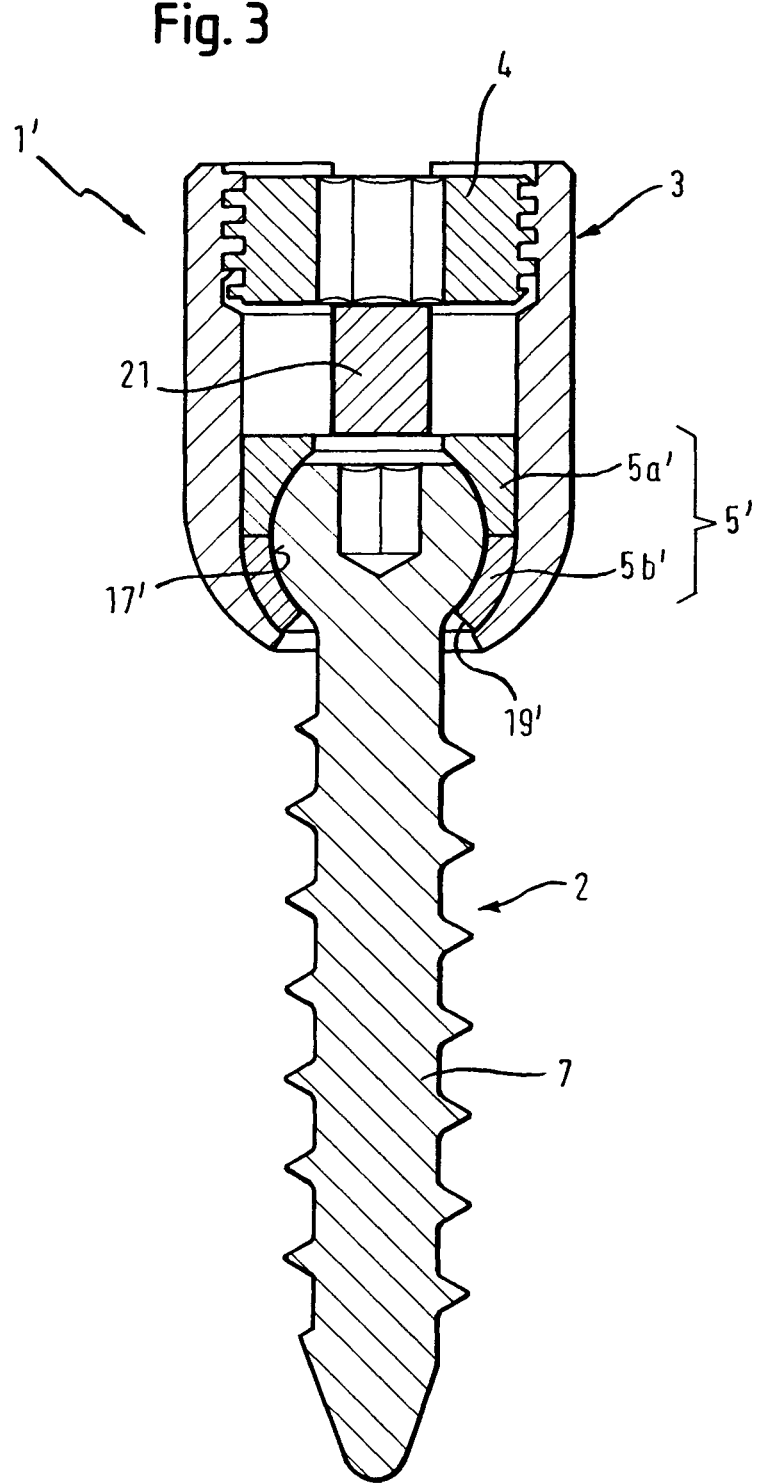

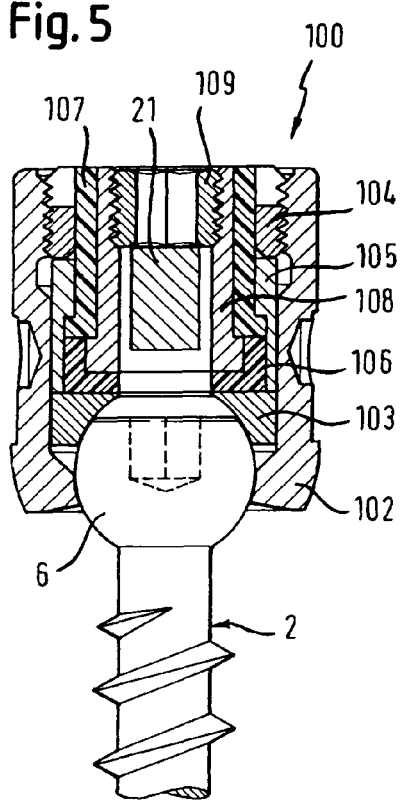
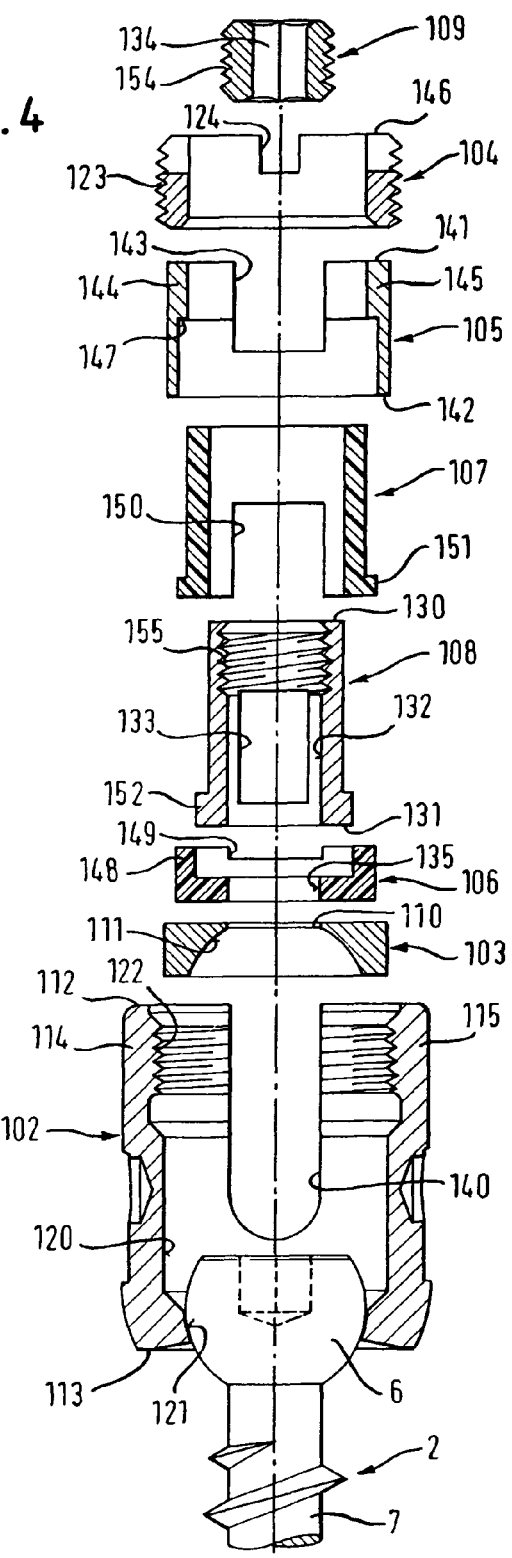

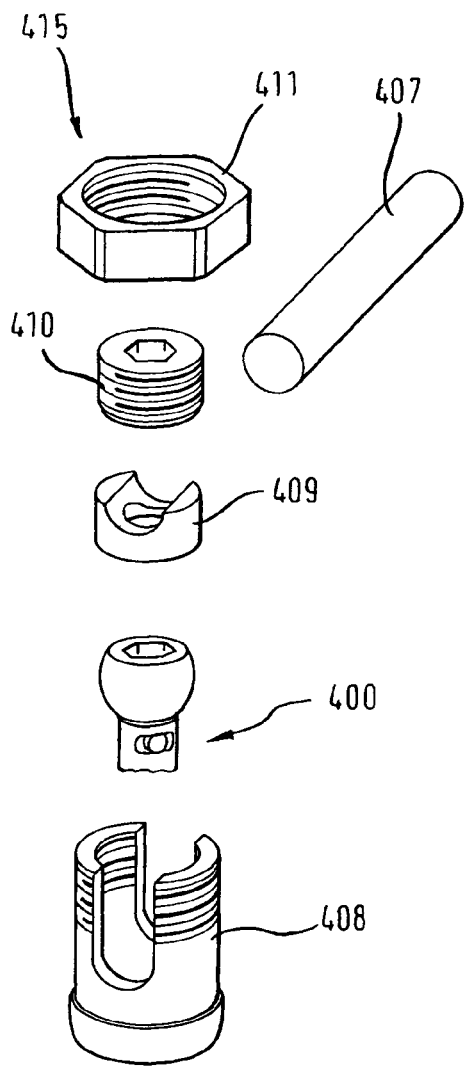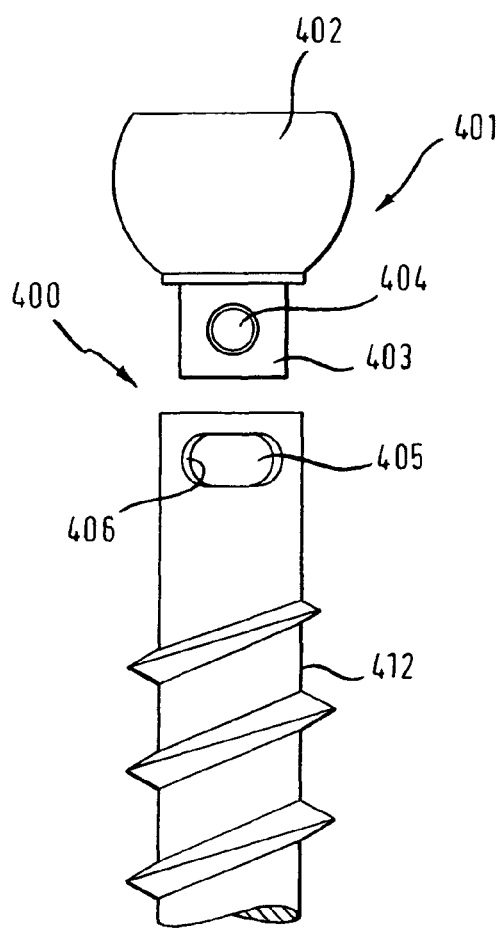

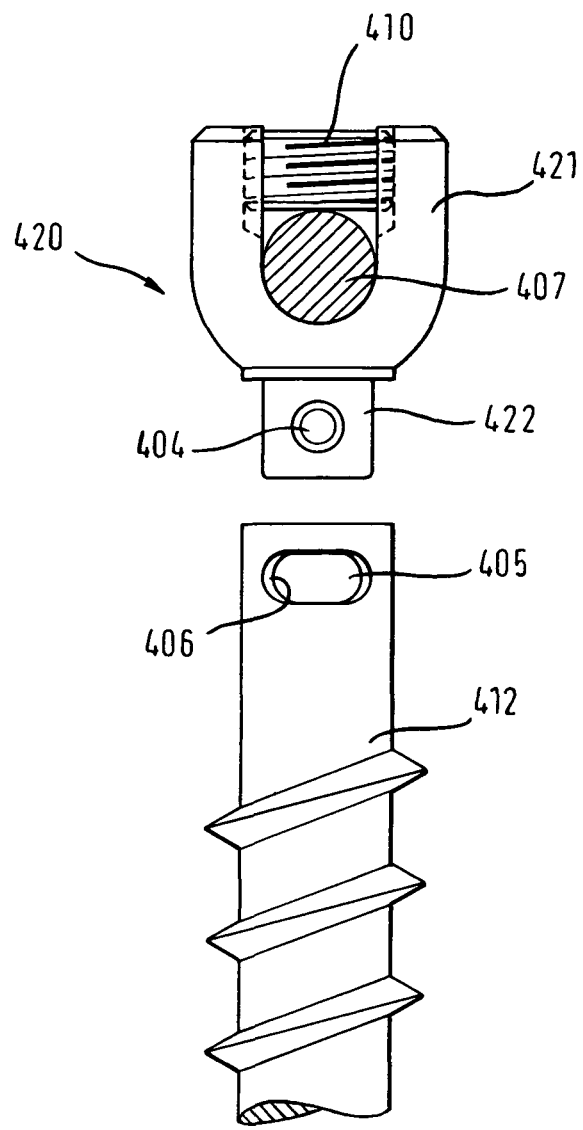

ANCHORING ELEMENT AND STABILIZATION DEVICE FOR THE DYNAMIC STABILIZATION OF VERTEBRAE OR BONES USING SUCH ANCHORING ELEMENTS

REFERENCE TO EARLIER FILED APPLICATIONS

The present invention claims the benefit of the filing date under 35 U.S.C. §119(e) of Provisional U. S. patent application Ser. No. 60/550,008, filed Mar. 3, 2004, which is hereby incorporated by reference in its entirety. The present application also claims foreign priority benefits pursuant to 35 U.S.C. §119 (a)-(d) for German Patent Application 10 2004 010 380.1, filed Mar. 3, 2004 in Germany.

BACKGROUND

The present invention relates to an anchoring element and a stabilization device for the dynamic stabilization of vertebrae or bones using such anchoring element.

Rigid fixation and stabilization devices for the fixation of bone fractures or for the stabilization of the spinal column are known. The conventional fixation and stabilization devices often consist of two bone screws that are each anchored in a bone and/or vertebra and are connected to each other by means of a rigid rod. For example, European Patent, EP 0 483 242, describes an anchoring element, which is used in conjunction with a rigid rod as a stabilization device. Rigid systems are generally used where any relative motion of the bone parts or vertebrae to be stabilized with respect to each other is not desirable, such as for example, in the case of bone fractures or other bone defects.

A bone anchoring element in the form of a polyaxial bone screw with a screw element and a receiving part for connection to a rod is known from U.S. Pat. No. 5,474,555 ('555 Patent). The '555 Patent describes a screw element to be anchored in the bone which is connected to the receiving part so that there is some motion between the screw element and the receiving part. However, the '555 Patent does not allow for stabilization of the bone with the possibility or option of controlled motion.

In certain clinical indications, such as damaged intervertebral disks or in the presence of an artificial intervertebral disk, it is desirable to have a stabilization device enabling the vertebrae to be stabilized and yet having some limited motion. A dynamic stabilization device of this type is known, for instance, from U.S. Pat. No. 5,733,284.

These known stabilization devices, in particular the dynamic devices, are associated with the inherent risk that the rod may exert a torque onto the anchoring element. This can eventually lead to the anchoring element loosening and/or separating from the bone, and thus the stabilizing device becoming ineffective.

FIG. 9 shows the generation of a torque M around the screw axis in a conventional stabilization device 200. In this stabilization device 200 shown therein, two bone anchoring elements 202, 202' are connected to each other by means of a curved rod 201 with a predetermined bending elasticity. Bone anchoring elements 202, 202' are firmly anchored in two neighboring vertebrae (not shown) by means of bone screws. FIG. 9 illustrates what occurs when the two bone anchoring elements 202, 202' are pressed together by a force F. Due to the force F, a bending moment is exerted onto the rod, which leads to a torque M around the screw axis acting on bone anchoring elements 202, 202'. Similarly, pulling the two bone anchoring elements apart with a force F leads to a torque M in the opposite direction around the screw axis. Both of these types of forces can lead to the loosening or separation of the bone anchoring element from the bone and/or vertebrae.

It is therefore an object of the present invention to provide an anchoring element and a dynamic stabilization device for the stabilization of the bone with limited motion of neighboring vertebrae or bones, in which the anchoring element is prevented from loosening or separating during operation.

BRIEF SUMMARY

This invention relates to an anchoring element for anchoring a rod-shaped element in the bone or vertebrae comprising a shaft to be anchored in the bone or vertebrae, a receiving part connected to the shaft for receiving a rod-shaped element, a fixation device for fixing the rod shaped element into the receiving part, wherein the shaft is connected by means of the receiving part to the rod-shaped element in a mobile fashion so that the shaft can move with respect to the rod-shaped element with at least one degree of rotational freedom but no degree of translational freedom.

This invention also relates to an anchoring element for anchoring a rod-shaped element in the bone or vertebrae comprising anchoring means such as a hook to be anchored in the bone or vertebrae, a receiving part connected to the shaft for receiving a rod-shaped element, a fixation device for fixing the rod shaped element into the receiving part, wherein the shaft is connected by means of the receiving part to the rod-shaped element in a mobile fashion so that the shaft can move with respect to the rod-shaped element with at least one degree of rotational freedom but no degree of translational freedom.

This invention further relates to anchoring element which comprises a screw element, a receiving part, a pressure element, a first ring, a second ring, a first bearing part, a second bearing part, a rod mounting, an internal screw and a rod shaped element. With these components, a connection is obtained between the rod shaped element and the bone in which the rod mounting with the rod shaped element can rotate in a predetermined range of angles around the main axis of the receiving part.

By making the connection of the section of the anchoring element that is anchored in the bone capable of rotating relative to the rod, the anchoring element of the present invention can be prevented effectively from loosening or separating under the action of torque acting on the anchoring element. The stabilization device is advantageously used for uncoupling the shaft rotation of the head or rod fixation in the dynamic stabilization of vertebrae.

The foregoing paragraphs have been provided by way of general introduction, and are not intended to limit the scope of the following claims. The presently preferred embodiments, together with further advantages, will be best understood by reference to the following detailed description taken in conjunction with the accompanying drawings.

BRIEF DESCRIPTION OF THE DRAWINGS

FIG. 1a shows an exploded view of an anchoring element according to a first embodiment of the invention;

FIG. 1b shows a partial sectional view of the anchoring element according to the first embodiment of the invention with a rod inserted;

FIG. 2 shows a perspective view of a bearing part used in the first embodiment of the invention;

FIG. 3 shows a modification of the anchoring element according to the first embodiment;

FIG. 4 shows an exploded view of an anchoring element according to a second embodiment of the invention;

FIG. 5 shows a partial sectional view of the anchoring element according to the second embodiment of the invention;

FIG. 8a shows an exploded view of an anchoring element according to a third embodiment of the invention;

FIG. 8b shows a bone screw with rotatable connection between head and anchoring section as used in the third embodiment of the invention;

FIG. 8c shows a modification of the anchoring element according to FIGS. 8a and 8b.

DETAILED DESCRIPTION OF THE DRAWINGS AND PRESENTLY PREFERRED EMBODIMENTS

Figure 6A:
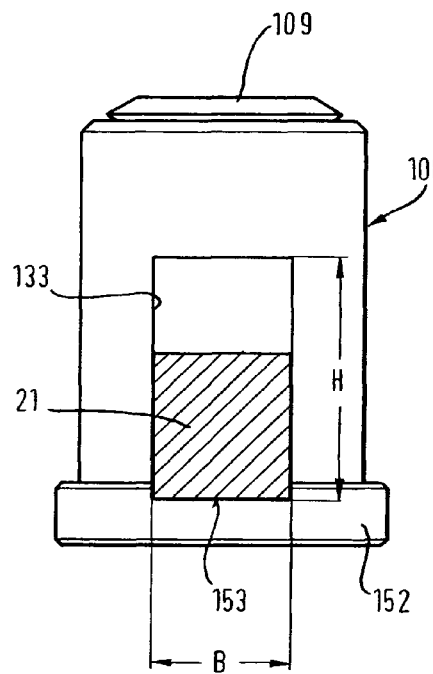
FIG. 6a shows a side view of the rod mounting of the anchoring element according to the second embodiment with a rod inserted and with the internal screw not yet fully tightened.

The invention and various embodiments thereof are presented in FIGS. 1 to 8 and the accompanying descriptions wherein like numbered items are identical.

As is evident from FIGS. 1a and 1b, according to a first embodiment, an anchoring element 1 for connecting a bone part or a vertebra and a rod 21, preferably with a rectangular cross-section, comprises a screw element 2, a receiving part 3, an internal screw 4 to be screwed into the receiving part and a bearing part 5.

The screw element 2 comprises a spherical segment-shaped head 6 and a thread shaft 7 for anchoring in the bone or vertebra. Although shown as spherical segment shaped, it will be appreciated by those skilled in the art that the head can be of other shapes provided that it can be received into the receiving part 3. On the side facing away from thread shaft 7, head 6 of screw element 2 is flattened and includes a recess 8 for engagement of a hexagon socket screw key. It will be appreciated by those skilled in the art that the recess can be any shape desired provided an insertion tool, such as for example, a hex socket screw key can be used therewith.

Receiving part 3 is an essentially cylindrically-shaped body with a first end 9 and a second end 10 opposite to the first end. The receiving part includes a bore hole 11 that extends coaxially to the main axis of the receiving part. Adjacent to first end 9 is a rectangular recess 12 for receiving the rod 21, with said recess forming two free legs 40, 41. Preferably, the width of the recess is slightly larger than the length of the narrow side of the rod, whereas the depth of the recess is slightly larger than the length of the broad side of the rod. Although described as an essentially cylindrically shaped body, the receiving part can be of any shape provided that it can receive the head of the screw as well as the rod. An internal thread 13 is provided in the bore hole 11 on the inside of legs 40, 41 adjacent to the first end 9. The bore hole 11 has an essentially constant internal diameter within a first section that is adjacent to the first end with said diameter being larger than the diameter of head 6 of screw element 2. Adjacent to the first section, receiving part 3 comprises a section that tapers in the direction from first end 9 to second end 10 such that a spherical seat or a ledge 14 is formed that is adjacent to the second end. The orifice 32 on the side of the second end is larger than the diameter of thread shaft 7 of screw element 2.

The bearing part 5 comprises a cylindrical section 30 with a flat front side 15. The diameter of the cylindrical section is selected so that in the assembled state, this section is press-fit and resides in the first section of receiving part 3. Moreover, bearing part 5 comprises a ball socket-shaped section 31 adjacent to its cylindrical section with the outer shape of section 31 corresponding to the shape of spherical seat 14. Inside bearing part 5 is a spherical recess 17 which serves to receive head 6 of screw element 2 and corresponds to the spherical shape thereof. Depending on the desired resistance to the rotation and pivoting motion of the screw element relative to the bearing part, the internal diameter of recess 17 can be made approximately equal or just slightly larger than the diameter of the head of the screw element. A bore hole 18 extends from the flat front side 15 and ends in recess 17. The bore hole 18 preferably has a diameter which allows a hexagon socket screw key to be inserted therein for tightening of the screw element 2, but is smaller than the diameter of head 6 of screw element 2. In the ball socket-shaped section of the bearing part 5, a coaxial bore hole 19 extends through to recess 17, with the diameter of coaxial bore hole 19 being smaller than the diameter of head 6 of screw element 2, but larger than the diameter of thread section 7.

As is seen from FIG. 2, bearing part 5 further includes slits 20 in the ball socket-shaped section adjacent to the side of the bearing part that is opposite to the flat front side 15. The slits 20 increase the elasticity of the bearing part. Preferably, bearing part 5 is made from a body-compatible plastic material having beneficial gliding properties. Most preferably, polyethylene (PE) is used. PE has a broad range of molecular weights which depend upon the extent of cross-linking in the polymer. For example, LDPE (low density polyethylene) and LLDPE have molecular weights of up to 50,000 g/mol, HDPE (high density polyethylene) has molecular weights of up to 200,000 g/mol or UHMWP (Ultra-High Molecular Weight Polyethylene) with molecular weights of approx. 6,000,000 g/mol. Preferably UHMWP is used as the material for the bearing part due to its durability and low long-term wear and tear.

The internal screw 4 comprises a coaxial recess 42 for engagement of an insertion tool such as a hexagon socket screw key.

In operation, head 6 of screw element 2 is first inserted into recess 17 of bearing part 5 and then screw element 2 and bearing part 5 are inserted together into receiving part 3. Subsequently, screw element 2 is screwed into the bone or vertebra. Then rod-shaped element 21 is placed in receiving part 3 which causes receiving part 3 to align itself correctly with respect to rod-shaped element 21. Thereafter, rod-shaped element 21 is fixed with respect to receiving part 3 by means of internal screw 4.

According to the procedure described above, a connection between screw element 2, which is firmly screwed into the bone or vertebra, and rod-shaped element 21 is generated, in which head 6 of screw element 2 is seated in bearing part 5, so that it is rotatable in a predetermined range of spatial angles. The range of spatial angles can be determined by the diameter of thread shaft 7, on the one hand, and by the diameter of orifice 32 on the side of second end 10 of receiving part 3 or by the diameter of the coaxial bore hole 19 in bearing part 5 on the other hand. Depending on how the diameter of spherical recess 17 and the diameter of head 6 were selected relative to each other, different frictional forces acting between the head and the bearing part can be set. Therefore, the forces can be set, which need to be overcome in order to rotate or pivot head 6 of screw element 2 in recess 17 of bearing part 5.

FIG. 3 shows a modification of the anchoring element 1 according to the first embodiment in which the bearing part 5' is made from two pieces, a first bearing element 5a' and a second bearing element 5b'. The two-piece bearing part 5' is similar to bearing part 5, but is cut into two pieces parallel to the front side of bearing part 5. As there are two pieces, the head 6 of screw element 2 can be inserted into recess 17' without having to enlarge orifice 19'. Consequently, bearing part 5' can be made from a stiff material with no slits.

FIGS. 4 to 7 show an anchoring element 100 according to a second embodiment of the invention. As is best seen from FIGS. 4 and 5, anchoring element 100 of the second embodiment comprises a screw element 2, a receiving part 102, a pressure element 103, a first ring 104, a second ring 105, a first bearing part 106, a second bearing part 107, a rod mounting 108 and an internal screw 109.

Screw element 2 in the anchoring element 100 of the second embodiment is identical to screw element 2 of the anchoring element 1 according to the first embodiment.

Receiving part 102 is an essentially cylindrical body with a first end 112 and a second end 113 opposite to the first end. Although shown as essentially cylindrical, it will be appreciated by those of ordinary skill in the art that the receiving part 102 can be of other shapes, provided that it receives and holds the screw element 2. A coaxial bore hole 120 extends from first end 112 to second end 113 of receiving part 102. An essentially U-shaped recess 140 is provided adjacent to first end 112 and forms two free legs 114 and 115. An internal thread 122 is provided adjacent to first end 112 on the inside of free legs 114 and 115. Bore hole 120, located in a receiving part 102 in a first section that is adjacent to first end 112, has an essentially constant diameter which is larger than the diameter of head 6 of screw element 2. In a second section, which is adjacent to the first section and extends to the second end of receiving part 102, bore hole 120 tapers in the direction of second end 113. A spherical section or even a ledge 121 is provided adjacent to second end 113 whose shape is adapted conform or mate with the shape of head 6 of screw element 2. The diameter of the bore hole in the second section is selected so that next to the second end, it is smaller than the diameter of head 6, yet larger than the diameter of thread shaft 7 of screw element 2. Although shown in this manner, it will be appreciated by those of ordinary skill in the art, that the section 121 can be of any shape provided that it can support the screw head 6.

On its outside, first ring 104 comprises an external thread 123, which acts in conjunction with internal thread 122 on the inside of free legs 114 and 115 of receiving part 102. On the front side 146 of ring 104 recesses 124 extends in a radial direction and can be used to engage a tool for screwing-in first ring 104 into receiving part 102.

Second ring 105 is provided to be cylindrically shaped with a constant external diameter with a first section with a first internal diameter being adjacent to a first end 141 and a second section with a second internal diameter being adjacent to a second end 142 with the second internal diameter being larger than the internal diameter of the first section, so that a shoulder 147 is formed thereby. The external diameter of second ring 105 is constant along its entire length and slightly smaller than the diameter of bore hole 120 in the section adjacent to first end 112 of receiving part 102 such that second ring 105 can slide into bore hole 120. A rectangular recess 143 forming two free legs 144, 145 is provided adjacent to first end 141. The width of recess 143 is similar to the width of U-shaped recess 140 of receiving part 102 in that it is larger than the narrow side of the rectangular cross-section of the rod so that when rod 21 is placed in the recess 143, it can be pivoted back and forth through a predetermined range of angles, preferably about 10°.

The pressure element 103 essentially has the shape of a flat cylinder with a spherical recess 111 on the side facing the screw head, with the shape of the spherical recess being adapted to complement the shape of head 6 of screw element 2. The pressure element 103 is also provided with a coaxial bore hole 110, which ends in recess 111 and enables a screwdriver or other tool to be inserted into the bore hole 110. The external diameter of pressure element 103 is slightly smaller than the diameter of bore hole 120 in receiving part 102 so that pressure element 103 can slide into the bore hole of the receiving part of the receiving part.

The first and the second ring 104, 105 serve to exert a force on pressure element 103 and therefore fix head 6 of screw element 2 in spherical section 121.

First bearing part 106 has the shape of a circular disc with a coaxial bore hole 135 for guiding-through a screwdriver and with a ring-shaped projection 148, which extends along the direction of the circumference and, when completely assembled and inserted, resides on the side facing away from the pressure element. The ring-shaped projection comprises two rectangular recesses 149 opposite to each other. Although the first bearing part is shown in this manner, it will be appreciated by those of ordinary skill in the art that the first bearing part can be of any desired shape.

The second bearing part 107 is provided as a tube-shaped section with a flange-like overhang 151, wherein the diameter of the tube-shaped section is smaller than the diameter of first bearing part 106. The external diameter of flange-like overhang 151 of second bearing part 107 is identical to the diameter of first bearing part 106. Two rectangular recesses 150 are opposite to each other and adjacent to the side with flange-like overhang 151. Although the second bearing part is shown in this manner, it will be appreciated by those of ordinary skill in the art that the second bearing part can be of any desired shape.

In the assembled state, the first and the second bearing part 106, 107 are arranged coaxially so that ring-shaped projection 148 of first bearing part 106 is adjacent to flange-like overhang 151 of second bearing part 107, wherein the rectangular recesses 149, 150 in the two bearing parts 106, 107 are each aligned towards each other so that two orifices for receiving the rod are formed by the two bearing parts 106, 107 with said orifices being opposite to each other and ending in the inside of the bearing. The width of the orifices formed by recesses 149, 150 in the assembled state is designed so that the rod 21 placed through these orifices can be pivoted back and forth through a predetermined range of angles, preferably about 10°. The height of the orifices formed by recesses 149, 150 in the assembled state is slightly larger than the corresponding cross-sectional diameter of rod 21. The external diameter of the bearing parts is dimensioned just to enable the bearing to be press-fitted in the first and second rings 104, 105. In the assembled state, flange-like overhang 151 rests against the shoulder 147 of second ring 105. The rectangular recesses 149, 150 act as limit stops to limit the rotational motion.

Preferably, the first and the second bearing part 106, 107 are made from a body-compatible plastic material with beneficial gliding properties. Preferably, polyethylene (PE) is used. As described above, PE has a broad range of molecular weights which depend upon the extent of cross-linking in the polymer. Preferably, UHMWP is used as the material for the bearing part due to durability and its low long-term wear and tear. The remaining parts of the anchoring element are preferably made from a body-compatible material with beneficial mechanical properties, such as titanium. Examples of other body-compatible materials include body-compatible metals and body compatible plastics such as for example, but not limited to, stainless steel, titanium alloys, nickel-titanium alloys, nitinol, chrome alloy, cobalt chrome alloys, shape memory alloys, materials with super elastic properties, carbon reinforced composites, silicone, polyurethane, polyester, polyether, polyalkene, polyethylene, polyamide, poly(vinyl) fluoride, polyetheretherketone (PEEK), polytetrafluoroethylene (PTFE).

Figure 6B:
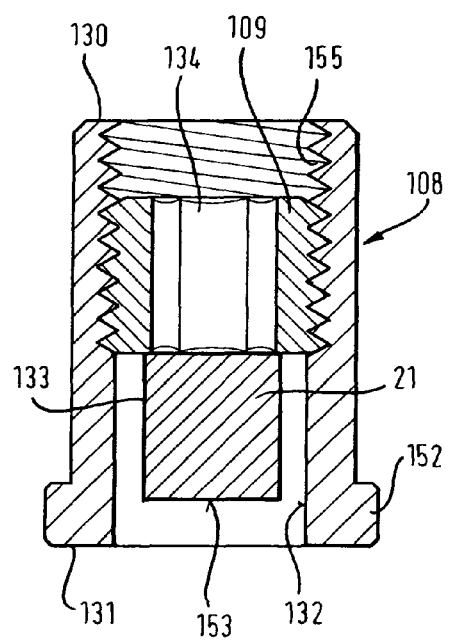
FIG. 6b shows a sectional view of the rod mounting of the anchoring element according to the second embodiment with a rod inserted and with the internal screw tightened.

As is evident from FIGS. 5, 6a, and 6b, the rod mounting 108 is provided as a cylinder-shaped body with a first end 130 and a second end 131. A continuous coaxial bore hole 132 extends from first end 130 to second end 131. An internal thread 155 is provided in bore hole 132 adjacent to first end 130, into which the internal screw 109 can be screwed into. The external diameter of the rod mounting 108 is slightly smaller than the internal diameter of second bearing part 107. On its second end 131, rod mounting 108 includes a flange-like overhang 152, whose external diameter is slightly smaller than the internal diameter of first bearing part 106. Two orifices 133 that are opposite to each other and have rectangular cross-sections are provided on the side walls of rod mounting 108. The width B of the orifice is slightly larger than the width of the rod. The height H of the orifice is larger than the height of the rod.

The internal screw 109 comprises an external thread 154 which acts in conjunction with the internal thread 155 of rod mounting 108. A coaxial bore hole 134 extending through internal screw 109 has a cross-section that is suitable for being engaged by a tool such as a hexagon socket screw key.

As is seen from FIGS. 6a and 6b, the axial length of internal thread section 155 of rod mounting 108 and the height of orifices 133 is selected so that the rod is displaceable from a first position, to a second position, while the rod is pressed against the lower edge 153 of orifice 133 and thereby fixed in position by tightening internal screw 109.

In operation, for preassembly of the anchoring element 100, screw element 2 is inserted into receiving part 102 first with thread shaft 7 leading so that head 6 rests on the ledge or section 121 of the receiving part. Subsequently, proceeding from first end 112 of receiving part 102, a pressure element 103 is inserted in coaxial bore hole 120 of receiving part 102, first with spherical recess 111 facing the head, followed by a first bearing part 106 being inserted into receiving part 102 with the coaxial bore hole leading. Then, rod mounting 108 with internal screw 109 is screwed-in is placed into first bearing part 106 but not completely tightened. Then, second bearing part 107 and second ring 105 are inserted one after the other between the side wall of receiving part 102 and the first and the second bearing part 106, 107. Finally, first ring 104 is screwed into receiving part 102 only so far as to prevent the elements thus inserted into receiving part 102 from falling out.

Alternatively, rod mounting 108, first and second bearing part 106, 107, first and second ring 104, 105 and internal screw 109 can be assembled outside of the receiving part first and then inserted into the receiving part. Other methods of assembly are also possible.

In operation, a hexagon socket screw key or other insertion tool is guided through the bore holes 134, 132, 135 and 110 and used during the surgery to turn and fasten screw element 102 into the vertebra or bone. Subsequently, proceeding from the side of receiving part 102, the rod is slid between the two free legs 114 and 115 of receiving part 102 through the orifices 133 in rod mounting 108 and through the orifices in the first and second bearing part 106 and 107 as well as through the recesses in first ring 105. Then, a force is exerted on pressure element 103 by tightening first ring 104. Then receiving part 102 is fixed in position relative to screw element 2. Thereafter, rod 21 is fixed in position in rod mounting 108 by inserting and tightening internal screw 109.

Figure 7A:
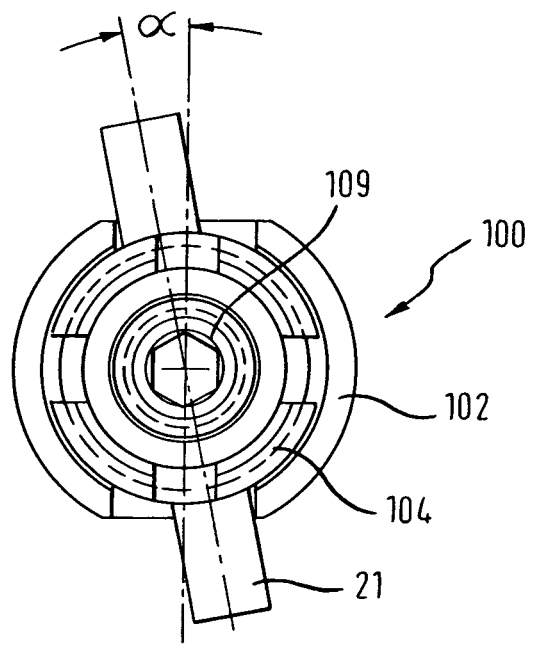
FIGS. 7a and 7b show an anchoring element according to the second embodiment of the invention in two different angle positions of the rod-shaped element relative to the receiving part.
Figure 7B:
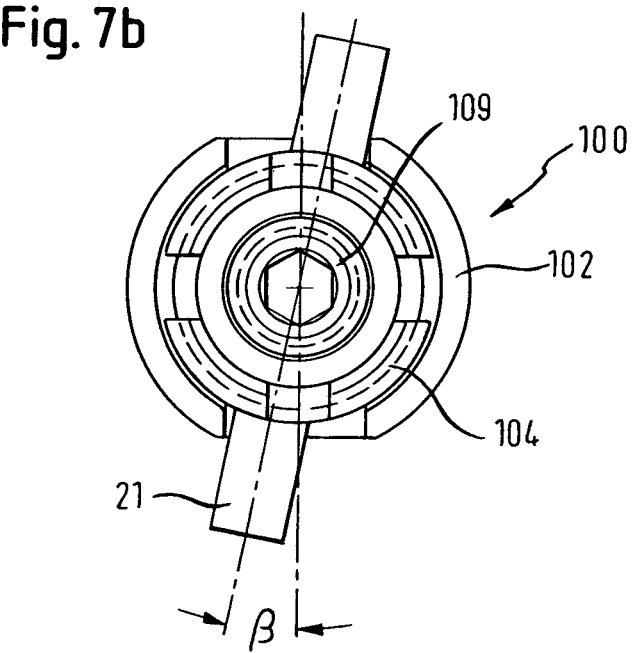
Figure 9:
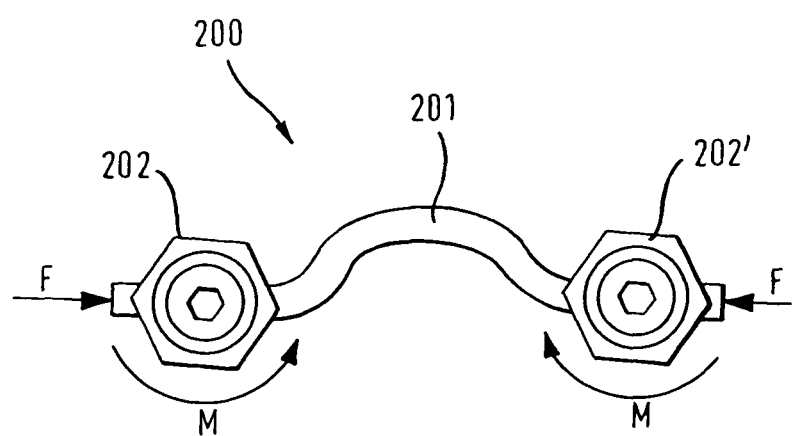
FIG. 9 shows the generation of a torque onto a bone screw in a conventional dynamic stabilization device.

This device effectively generates a connection between rod-shaped element 21 and the bone or vertebra, in which rod mounting 108 with the fixed rod-shaped element 21 can rotate in a predetermined range of angles around the main axis of receiving part 102. The range of angles is determined by the dimension of rod 21, the width of recess 140 in receiving part 102, the width of rectangular recesses 149, 150 in first and second bearing part 106, 107 of orifices 149 and the width of recesses 143 in second ring 105. Rod mounting 108 rotates jointly with rod 21, whereas bearing part 106, 107 are seated firmly in the first and second rings 104, 105 by press-fitting. The angle position of the screwing axis relative to the receiving part 102 remains fixed. FIGS. 7a and 7b show two different limit angle positions $\alpha$, $\beta$ of rod-shaped element 21 with respect to receiving part 102.

In contrast to anchoring element 1 of the first embodiment, in which the rod has three degrees of rotational freedom relative to the screw element, the connection with an anchoring element 100 according to the second embodiment has only one degree of rotational freedom relative to the screw element.

According to a third embodiment of the invention, a rotatable connection between a rod and a bone or vertebra is obtained by the use of a polyaxial screw, in which the angle between rod 407 and receiving part 408 and between screw element and receiving part is fixed. FIG. 8a, shows a two-piece screw element 400, in which the head 401 of the screw element is connected to the thread shaft 412 so that it is capable of rotation. As further shown in FIG. 8a, the polyaxial screw comprises a receiving part 408, a pressure element 409 an internal screw 410 and an external screw or nut 411.

As is evident from FIG. 8b, head 401 of screw element 400, consists of a spherically segment-shaped head section 402 with a cylindrical neck 403. A pin 404 is provided at the side surface of neck 403. The pin 404 can be pressed along its longitudinal axis into neck 403 against a spring force.

On its side facing the head 401 of screw element 400, threaded shaft 412 includes a coaxial recess 405. Neck 403 can be engaged in a coaxial recess 405. A longitudinal hole 406 is provided in the side wall of this recess 405, in which pin 404 can be engaged.

In operation, the pin is pressed into the neck so that neck 403 can slide into recess 405 of thread shaft 412. When neck 403 slides into recess 405, the outward pressure of the spring force of pin 404, engages longitudinal hole 406 in the wall of recess 405. This generates a connection between head 401 and thread shaft 412 of screw element 400, in which head 401 can be rotated coaxially with respect to thread shaft 412 of the screw element and thread shaft 412 of the screw element can be rotated coaxially with respect to each other through a range of angles that is predetermined by the length of the longitudinal hole 406.

Screw element 400 is then inserted into a receiving part 408 and screwed into the bone. Subsequently, the position of the screw element with respect to the receiving part is fixed, and rod 407 is inserted and fixed in a known fashion. As in the second embodiment, the connection to an anchoring element according to the third embodiment has one degree of rotational freedom.

In a modification of the third embodiment shown in FIG. 8c, bone anchoring element 420 is provided in the form of a monoaxial screw, in which the receiving part 421 is firmly connected to the head of the two-piece screw element or is an integral component thereof. In all other aspects, bone anchoring element 420 is identical to the bone anchoring element third embodiment described above.

Other modifications of the embodiments described are possible and contemplated.

For example, bore hole 19 of the anchoring element according to the first embodiment was described as having a diameter that is smaller than that of head 6 but larger than the diameter of thread section 7. However, the diameter of bore hole 19 can also be smaller than the diameter of thread section 7 so long as the screw element is provided in two pieces so that there is no need to guide the threaded shaft through bore hole 19 during assembly. It shall also be possible to provide the bore hole so that the screw element can be screwed through the bore hole.

In the anchoring element according to the first embodiment, the head can have a non-spherical but rotationally symmetrical shape with respect to the screw axis and it can restrict the rotational motion of the screw element relative to the receiving part to one degree of freedom. Further, bearing part 5 according to the first embodiment need not necessarily include one or more slits 20 provided the elasticity of the material used for the bearing part allows for the insertion of head 6 of screw element 2 in the absence of slits 20.

The diameter of bore hole 120 in the second section of receiving part 102 according to the second embodiment was described to be larger than the diameter of thread shaft 7 of screw element 2 in an area adjacent to second end 113. However, the diameter of bore hole 120 adjacent to the second end can also be dimensioned so that the screw element is screwed through the bore hole or, in the case of a multiple-piece screw element, the diameter of bore hole may be smaller than the diameter of thread shaft 7, which in this case does not need to be guided through bore hole 120 but rather is connected from the outside to the head residing in the receiving part.

In yet another modification of the invention, first bearing part 106 can also be provided without a projection 148.

Furthermore, the anchoring element 100 according to the second embodiment can be in the form of a monoaxial screw, that is firmly connected to screw element 2 or is an integral component thereof of the receiving part 102.

In all anchoring elements described above, a different type of anchoring element in the bone or vertebra can be used instead of a screw element 2. An example of a different type of anchoring element is a hook.

The bone anchoring elements according to the first and second embodiments of the invention were described for rod-shaped elements with a square cross-section. By adequately modifying the recesses and bore holes for receiving the rod, these bone anchoring elements can also be adapted to the use of rod-shaped elements with a circular or any other cross-section. Similarly, the bone anchoring element according to the third embodiment can be modified for the use with a rod-shaped element with a rectangular or any other cross-section.

The third embodiment describes a pin 404 that can be pressed into neck 403 against a spring force. However, pin 404 can also be inserted by press-fitting into a hole in neck 403 or 422 and thereby be firmly connected to neck 403 or 422. In this case, the neck is inserted into recess 405 without the pin, and then the pin is inserted through longitudinal hole 406 into the hole in the neck. It shall also be possible to provide the pin and the neck such that the pin has an external thread and can be screwed into an internal thread provided in the hole in the neck. A multiplicity of different rotary connections between screw head 401 and the thread section 402 shall also be possible.

The embodiments described above and shown herein are illustrative and not restrictive. The scope of the invention is indicated by the claims, including all equivalents, rather than by the foregoing description and attached drawings. The invention may be embodied in other specific forms without departing from the spirit and scope of the invention.

We claim:

1. A bone or vertebrae anchoring assembly, comprising:
   a rod-shaped element;
   an anchoring element comprising a head and a shaft, the shaft configured to be anchored to the bone or vertebra;
   a receiving part to connect the rod-shaped element to the shaft, the receiving part having a bore configured for simultaneously receiving the anchoring element and the rod-shaped element with the rod-shaped element passing through the receiving part;
   a fixation device to fix the rod-shaped element in the receiving part; and
   a bearing part having an outward facing surface that is configured to be press-fit at a location in the receiving part such that the bearing part is between the anchoring element and the fixation device;
   wherein, when the shaft is connected to the receiving part and when the rod-shaped element is immobilized with respect to the receiving part, the shaft is connected by the receiving part to the rod-shaped element in a mobile fashion and the press-fit connection permits the shaft to move with respect to the rod-shape element with at least one degree of rotational freedom, but no degree of translational freedom.

2. An anchoring assembly according to claim 1, wherein the head is held in the bearing part so that the head is capable of rotation relative to the rod-shaped element when the shaft is connected to the receiving part and when the rod-shaped element is immobilized with respect to the receiving part.

3. An anchoring assembly according to claim 1, wherein a limit stop is provided for limiting the at least one degree of rotational freedom between the shaft and the rod-shaped element when the shaft is connected to the receiving part and when the rod-shaped element is immobilized with respect to the receiving part.

4. An anchoring assembly according to claim 1, wherein the shaft to be anchored in the bone or vertebra includes a bone thread.

5. A stabilization device with at least two bone anchoring elements and a rod-shaped element to connecting to said bone anchoring elements, at least one bone anchoring element comprising:
   an anchoring element comprising a head and a shaft, the shaft configured to be anchored to the bone or vertebra;
   a receiving part to connect the rod-shaped element to the shaft, the receiving part having a bore configured for simultaneously receiving the anchoring element and the rod-shaped element with the rod-shaped element passing through the receiving part;
   a fixation device to fix the rod-shaped element in the receiving part; and
   a bearing part having an outward facing surface that is configured to be press-fit at a location in the receiving part such that the bearing part is between the anchoring element and the fixation device;

wherein, when the shaft is connected to the receiving part and when the rod-shaped element is immobilized with respect to the receiving part, the shaft is connected by the receiving part to the rod-shaped element in a mobile fashion and the press-fit connection permits the shaft to move with respect to the rod-shaped element with at least one degree of rotational freedom, but no degree of translational freedom.

6. A method to assemble a bone anchoring assembly comprising a rod-shaped element, a screw element having a shaft to be anchored to a bone or vertebra and a head adjacent to the shaft, a bearing part with a recess and an outwardly facing surface, a receiving part having a bore that is configured to receive the rod-shaped element and the screw element, and fixation device to fix the rod-shaped element in the receiving part, the method comprising:

inserting the head of the screw element into the recess of the bearing part;

then press-fitting the outward facing surface of the bearing part into the receiving part and thereby connecting the head to the receiving part;

then fixing the rod-shaped element in an immobilized fashion to the receiving part while the shaft is connected by the receiving part to the rod-shaped element in a mobile fashion and the press-fit connection permits the shaft to move with respect to the rod-shaped element with at least one degree of rotational freedom, but no degree of translational freedom.

7. A method of using an anchoring assembly comprising a rod-shaped element, a screw element having a shaft and a head, a bearing part with a recess and an outwardly facing surface, a receiving part having a bore that is configured to receive the rod-shaped element and the screw element, a fixation device to fix the rod-shaped element in the receiving part, the method comprising:

inserting the head of the screw element into the recess of the bearing part;

then press-fitting the outward facing surface of the bearing part with said head of the screw element in its recess in the receiving part;

then inserting said screw element into the bone;

then fixing the rod-shaped element in an immobilized fashion to the receiving part while the shaft is connected by the receiving part to the rod-shaped element in a mobile fashion and the press-fit connection permits the shaft to move with respect to the rod-shaped element with at least one degree of rotational freedom, but no degree of translational freedom.

8. An anchoring assembly according to claim 1, wherein said head is integrally connected to said shaft.

* * * * *

UNITED STATES PATENT AND TRADEMARK OFFICE
CERTIFICATE OF CORRECTION

| | | |
|---|---|---|
| PATENT NO. | : 8,808,330 B2 | |
| APPLICATION NO. | : 11/070873 | |
| DATED | : August 19, 2014 | |
| INVENTOR(S) | : Lutz Biedermann et al. | |

It is certified that error appears in the above-identified patent and that said Letters Patent is hereby corrected as shown below:

In the Specification

Column 2, line 34          After "to" Insert -- an --

Column 5, line 44          Before "conform" Insert -- to --

Column 7, line 52          After "screwed-in" Insert -- and --

In the Claims

Column 10, Claim 1, line 36          Delete "rod-shape" Insert -- rod-shaped --

Column 10, Claim 4, line 51          Delete "in" Insert -- to --

Column 10, Claim 5, line 54          Delete "connecting" Insert -- connect --

Column 11, Claim 6, line 17          Before "fixation" Insert -- a --

Column 11, Claim 6, line 22          Delete "into" Insert -- in --

Signed and Sealed this
Sixth Day of October, 2015

Michelle K. Lee
*Director of the United States Patent and Trademark Office*